United States Patent [19]

Deline

[11] Patent Number: 6,017,464
[45] Date of Patent: Jan. 25, 2000

[54] DIMERIC N-ALKYL AMMONIUM ACETONITRILE BLEACH ACTIVATORS

[75] Inventor: James E. Deline, Livermore, Calif.

[73] Assignee: The Clorox Company, Oakland, Calif.

[21] Appl. No.: 09/207,797

[22] Filed: Dec. 9, 1998

Related U.S. Application Data

[60] Division of application No. 09/059,112, Apr. 13, 1998, Pat. No. 5,877,315, which is a continuation-in-part of application No. 08/475,292, Jun. 7, 1995, Pat. No. 5,739,327.

[51] Int. Cl.[7] .................................................. C09K 3/00
[52] U.S. Cl. .............................. 252/186.39; 252/186.38; 510/312
[58] Field of Search ..................... 252/186.39, 186.38; 510/312

[56] References Cited

U.S. PATENT DOCUMENTS

| | | |
|---|---|---|
| 2,425,693 | 8/1947 | Cook et al. . |
| 2,489,950 | 11/1949 | Blicke . |
| 2,625,547 | 1/1953 | Lawson et al. . |
| 2,774,758 | 12/1956 | Yanko . |
| 2,848,450 | 8/1958 | Rudner et al. . |
| 2,851,458 | 9/1958 | Billinghurst . |
| 2,868,786 | 1/1959 | Siemer et al. . |
| 3,532,735 | 10/1970 | Morgan . |
| 3,689,470 | 9/1972 | Shachat et al. . |
| 3,772,275 | 11/1973 | Hernestam et al. . |
| 3,780,092 | 12/1973 | Samour et al. . |
| 3,873,583 | 3/1975 | Walz et al. . |
| 3,882,035 | 5/1975 | Loffelman et al. . |
| 4,086,175 | 4/1978 | Kravetz et al. . |
| 4,134,889 | 1/1979 | Distler et al. . |
| 4,164,511 | 8/1979 | Distler et al. . |
| 4,199,466 | 4/1980 | Benson, Jr. . |
| 4,215,003 | 7/1980 | Finley et al. . |
| 4,328,226 | 5/1982 | Witek et al. . |
| 4,342,872 | 8/1982 | Grier et al. . |
| 4,397,757 | 8/1983 | Bright et al. . |
| 4,551,526 | 11/1985 | Mai et al. . |
| 4,737,498 | 4/1988 | Banasiak et al. . |
| 4,751,015 | 6/1988 | Humphreys et al. . |
| 4,904,406 | 2/1990 | Darwent et al. . |
| 4,915,863 | 4/1990 | Aoyagi et al. . |
| 4,921,631 | 5/1990 | Gradwell et al. . |
| 4,978,770 | 12/1990 | Aoyagi et al. . |
| 5,093,022 | 3/1992 | Sotoya et al. . |
| 5,106,528 | 4/1992 | Francis et al. . |
| 5,236,616 | 8/1993 | Oakes et al. . |
| 5,281,361 | 1/1994 | Adams et al. . |
| 5,330,677 | 7/1994 | Sotoya et al. . |
| 5,399,746 | 3/1995 | Steiger et al. . |
| 5,405,412 | 4/1995 | Willey et al. . |
| 5,460,747 | 10/1995 | Gosselink et al. . |
| 5,591,378 | 1/1997 | Deline et al. . |
| 5,741,437 | 4/1998 | Arbogast et al. ................... 252/186.39 |

FOREIGN PATENT DOCUMENTS

| | | |
|---|---|---|
| 883075582 | 8/1988 | European Pat. Off. . |
| A20303520 | 8/1988 | European Pat. Off. . |
| 912011707 | 5/1991 | European Pat. Off. . |
| 0790244 | 2/1997 | European Pat. Off. . |
| P25035829 | 1/1975 | Germany . |
| P25557691 | 12/1975 | Germany . |
| P26204455 | 5/1976 | Germany . |
| 62-225871 | 9/1987 | Japan . |
| 63-167157 | 7/1988 | Japan . |
| 1230773 | 9/1989 | Japan . |
| 6136391 | 10/1992 | Japan . |
| 96/07650 | 3/1996 | WIPO . |

OTHER PUBLICATIONS

Hart et al., "Some New Quaternary—Substituted Alkyl Morpholinium Chlorides and Pyrrolidinium Alkyl Sulfates," *Journal of Organic Chemistry*, 22:1 (Mar. 5, 1957), pp. 86–88.

Gubanova et al., "Synthesis and Antiviral Activity of Organic and Organophosphorus Derivatives of α–Aminonitriles," translated from *Khimiko–farmatsevticheskii Zhurnal*, 26, No. 7–8, pp. 60–62 (1992).

Stanley et al., "Synthesis and Enzymatic Evaluation of Some N–Alkyl Branched Chain Piperidine Salts and N–Alkyl–3–(N,N–diethylcarbamoyl)piperidine Salts as Inhibitors of Acetyl–and Butyrylcholinesterase," *J. Medicinal Chemistry*, 17, No. 1, (1974).

Lespagnol et al., "Guanidines monosubstituées à fonction ammonium quaternaire," *Mèmoires Prèsentès a la Societè Chimique*, paper presented at the Congress of the International Pharmaceutical Federation, Zurich, Sep. 1959.

*Primary Examiner*—Robert W. Ramsuer
*Attorney, Agent, or Firm*—Majestic, Parsons, Siebert & Hsue P.C.

[57] ABSTRACT

Bleaching compositions are provided that comprise two nitrile groups where each nitrile is bonded to a quaternary nitrogen through a methylene unit. The quaternary nitrogens are part of a saturated ring. This saturated ring contains from two to eight atoms in addition to the quaternary nitrogen. A source of active oxygen will react with the nitrites for bleaching applications.

6 Claims, No Drawings

DIMERIC N-ALKYL AMMONIUM ACETONITRILE BLEACH ACTIVATORS

This is a division of application Ser. No. 09/059,112, filed Apr. 13, 1998, now U.S. Pat. No. 5,877,315; which was in part a continuation-in-part of application Ser. No. 08/475,292, filed Jun. 7, 1995, now U.S. Pat. No. 5,739,327, issued Apr. 14, 1998.

FIELD OF THE INVENTION

The present invention generally relates to dimeric N-alkyl ammonium acetonitrile compounds, particularly for use as activators for hydrogen peroxide in bleaching and cleaning applications.

BACKGROUND OF THE INVENTION

Peroxy compounds are effective bleaching agents, and compositions including mono- or di-peroxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid can present a problem of storage stability for compositions consisting of or including peroxyacids.

One approach to the problem of reduced bleaching activity of peroxyacid compositions has been to include activators of peroxyacids. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester.

U.S. Pat. No. 4,778,618, Fong et al., issued Oct. 18, 1988 provides novel bleaching compositions comprising peracid precursors with the general structure

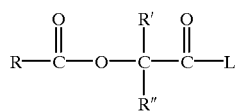

wherein R is $C_{1-20}$ linear or branched alkyl, alkylethoxylated, cycloalkyl, aryl, substituted aryl; R and R″ are independently H, $C_{1-20}$ alkyl, aryl, $C_{1-20}$ alkylaryl, substituted aryl, and $N^{+R_3^\alpha}$, wherein $R^\alpha$ is $C_{1-30}$ alkyl; and where L is a leaving group which can be displaced in a peroxygen bleaching solution by peroxide anion. U.S. Pat. No. 5,182,045, issued Jan. 26, 1993, and U.S. Pat. No. 5,391,812, issued Feb. 21, 1995, inventors Rowland et al. are similar, but are polyglycolates of the Fong et al. monoglycolate precursors, or activators.

U.S. Pat. No. 4,915,863, issued Apr. 10, 1990, inventors Aoyagi et al., discloses compounds said to be peracid precursors that have nitrile moieties. U.S. Pat. No. 5,236,616, issued Aug. 17, 1993, inventors Oakes et al., discloses compounds said to be cationic peroxyacid precursors that have nitrile moieties. These nitrile containing activators do not contain a leaving group, such as the Fong et al. leaving groups, but instead include a quaternary ammonium group suggested as activating the nitrile and said, upon hydrolysis in the presence of hydrogen peroxide, to generate a peroxy imidic acid as bleaching species. The Aoyagi et al. activators include an aromatic ring, which tends to cause fabric yellowing.

Thus, new peroxygen activators that do not gray or harm fabrics and that provide superior bleaching remain desirable for laundry and household bleaching and cleaning applications, such as laundry detergents, laundry bleaches, hard surface cleaners, toilet bowl cleaners, automatic dishwashing compositions, and the like.

SUMMARY OF THE INVENTION

In one aspect of the present invention, novel dimeric nitrile compounds are provided that have the Formula 1 and 2 structures:

FORMULA 1

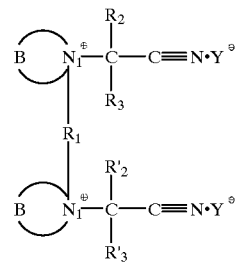

FORMULA 2

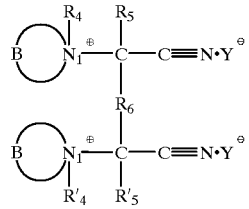

In both the Formula 1 and 2 structures, B is a saturated ring formed by a plurality of atoms in addition to the $N_1$ atom, and the ring atoms preferably include at least one carbon atom and at least one of 0, S, and N atoms, but can be composed of the one $N_1$ atom and the rest carbons. In Formula 1, $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. Particularly preferred Formula 1 compounds are useful as activators for hydrogen peroxide in bleaching and cleaning applications, in which case at least one of $R_2$ and $R_3$ is hydrogen and preferably where at least one of the Formula 1 dimer structure has $R'_2$ and $R'_3$ chosen from the same group of moieties as $R_2$ and $R_3$, and these may be the same as $R_2$ and $R_3$ or be different. In Formula 2, $R_5$ and $R'_5$ are analogous to $R_2$ and $R'_2$ of Formula 1, and preferably are chosen from the same group of moieties.

The $R_1$ linking group of Formula 1 is bonded to the $N_1$ atoms and includes a polyoxyalkylene group with 1 to 24 oxyalkylene units or an alkylene group with 1 to 24 carbons, as well as thioethers. In Formula 2, the linking group is $R_6$ and is linked to the α-carbon with respect to the cyano carbon. This α-carbon is a methylene carbon since greater numbers of carbon between the quaternary $N_1$ and the cyano carbon are believed to be disadvantageous for bleaching applications.

Since the Formula 1 and 2 compounds have quaternary nitrogen atoms ($N_1$), appropriate counterions (Y) will be associated therewith.

Compositions of the invention are useful as or in laundry products, such as bleaching additives, detergents, detergent boosters, detergents with bleach, bleaches, bleaching aids, stain removers, and spot treatment products such as stain removers, prewash and presoak laundry aids.

Detailed Description of the Preferred Embodiments

Broadly, the subject invention provides dimeric N-alkyl ammonium acetonitrile compounds having saturated rings that include quaternized nitrogen atoms and to which cyano groups are bonded through a single carbon atom (hereinafter sometimes the "α-carbon"). A linker joins the monomeric units, where each monomeric unit has a cyano group. The position of the linker is either between the quaternized nitrogens of the rings or between the α-carbons. Compounds of the subject invention most preferably have a hydrogen substituent on the α-carbon.

Formula 1 illustrates a dimeric embodiment of the invention when the linker is between quaternized nitrogens of the saturated rings, while Formula 2 illustrates dimeric embodiments where the linker is between the α-carbons adjacent to the cyano groups.

FORMULA 1

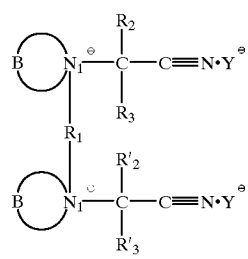

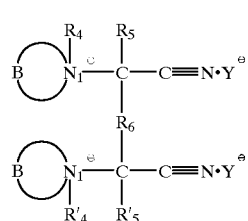

FORMULA 2

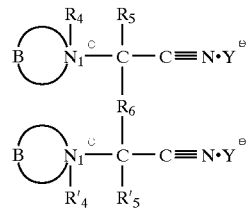

Formula 1 illustrates dimeric embodiments of the invention where $R_1$ is a linking group, which linking group $R_1$ may be a polyoxyalkylene group with 1 to 24 oxyalkylene units, such as groups derived from ethylene oxide, propylene oxide, butylene oxide, or mixtures thereof. Examples are:

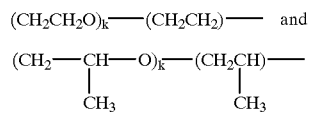

where k=1 to 24. Thioethers may also be used. The $R_1$ linking group may also be an alkylene group with 1 to 24 carbons.

$R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. $R'_2$ and $R'_3$ are chosen from the same group of moieties as $R_2$ and $R_3$, and may be the same as $R_2$ and $R_3$ or be different. More preferably, at least one of $R_2$ and $R_3$ and at least one of $R'_2$ and $R'_3$ are hydrogen. $R_4$ and $R'_4$ which may be the same or different, are a $C_{1-24}$ alkyl or alkoxylated alkyl where the alkoxy is $C_{2-4}$, a $C_{4-24}$ cycloalkyl, a $C_{7-24}$ alkaryl, a repeating or nonrepeating alkoxy or alkoxylated alcohol, where the alkoxy unit is $C_{2-4}$, and illustrative such groups are, for example,

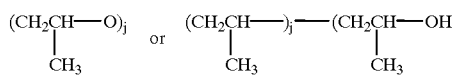

where j=1 to 24. The $R_4$ and $R'_4$ substituent may also be another $-CR_2R_3C\equiv N$, and again $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$, and illustrative such groups are:

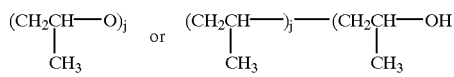

where j=1 to 24.

Formula 2 illustrates dimeric embodiments of the invention where $R_6$ is a linking group. This linking group, $R_6$, may be an alkylene $-[CH_2]_n-$ where n is 1 to about 15.

$R_5$ and $R'_5$ are each H, a $C_{1-24}$ alkyl, cycloalkyl, or alkaryl, or a repeating or nonrepeating alkoxyl or alkoxylated alcohol where the alkoxy unit is $C_{2-4}$. More preferably, at least one of $R_5$ and $R'_5$ is hydrogen.

Particularly preferred, saturated rings forming the cyclic configuration B of Formulas 1 and 2 have six atoms including the $N_1$ atom, but the number of atoms forming the cyclic configuration can range from 3 to 9. However, when two heteroatoms are present in the cyclic configuration B of Formulas 1 and 2, then a three member ring is unusual.

Where the saturated ring B of the Formula 1 and 2 structures includes two N atoms, then the second N atom, designated $N_2$, may be a secondary amine, a tertiary amine, or a quaternary amine.

Counterions

Since dimeric compounds of the invention are quaternized, they will include counterions (designated as "Y"), which can be monovalent or multivalent. Y includes organic and inorganic anions, such as, but not limited to, chloride, bromide, nitrate, alkyl sulfate, bisulfate, sulfate, tosylate, mesylate, and mixtures thereof.

Another preferred embodiment is wherein the counterions are selected from a class of anionic activators. For example, if the Formula I or Formula II nitriles are admixed with anionic bleach activators such as are described by U.S. Pat. No. 4,412,934 and by U.S. Pat. No. 4,778,618 (or are used to form ion pairs with the quaternized nitriles), then coactivation will occur when such are dissolved in an aqueous solution in the presence of an active oxygen source. Particularly preferred such coactivator embodiments are wherein the Y counterions have the Formula IV or Formula V structure.

FORMULA IV

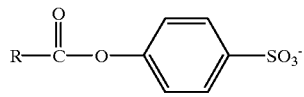

wherein R is a linear or branched alkyl chain containing from about 5 to about 9, and preferably from about 6 to about 8, carbon atoms.

FORMULA V

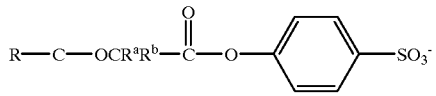

where $R^a$ and $R^b$=H, $CH_3$, ∅, OH; R=$CH_3(CH_2)_m$, m=0–24, or ∅; as understood, the $SO_3^-$ could conveniently be any other anionic substituent. This embodiment is described in copending application Ser. No. 08/758,545, filed Nov. 29, 1996, of common assignment herewith.

As already noted, compounds having the Formula 1 and Formula 2 structures have a saturated ring formed by a plurality of atoms, broadly ranging from 3 to 9, although preferably containing 6 atoms including the $N_1$ atom. Preparation of these compounds will most conveniently start with a compound already having the formed ring. For example, a number of preparations of inventive nitriles hereinafter described will begin with morpholine. An example of three membered rings is aziridine, e.g., N-methylacetonitrile aziridinium; as an example of four membered rings there is azetidine, e.g., N-ethylacetonitrile azetidinium; as an example of five membered rings there is pyrrolidine, e.g., N-butylacetonitrile pyrrolidinium; as an example of six membered rings, in addition to morpholine, there is piperidine, e.g., N-methylacetonitrile piperidinium; as an example of seven membered rings there is homopiperidine, e.g., N-ethylacetonitrile homopiperidinium; as an example of eight membered rings there is tropane, e.g., N-methylacetonitrile-8-azabicyclo[3.2.1]octane; and, as an example of nine membered rings there is octahydroindole, e.g., N-methylacetonitrile octahydroindolinium.

In general, N-quaternary acetonitrile compounds are readily prepared from N-acetonitrile precursors by employing selected alkyl halides and using well-known synthetic approaches, such as are described by Menschutkin, *Z. Physik. Chem.*, 5, 589 (1890), and *Z.*

Physik. Chem., 6, 41 (1890); Abraham, *Progr. Phys. Org. Chem.*, 11, 1 (1974); and Arnett, *J. Am. Chem. Soc.*, 102, 5892 (1980).

Bleaching and Cleaning Compositions

Bleaching and cleaning compositions of the invention include the dimer nitrites as activator, together with a source of active oxygen.

The peroxide or active oxygen source for compositions of the invention may be selected from the alkaline earth metal salts of percarbonate, perborate, persilicate and hydrogen peroxide adducts and hydrogen peroxide. Most preferred are sodium percarbonate, sodium perborate mono- and tetrahydrate, and hydrogen peroxide. Other peroxygen sources may be possible, such as monopersulfates and monoperphosphates. In liquid applications, liquid hydrogen peroxide solutions are preferred, but the activator may need to be kept separate therefrom prior to combination in aqueous solution to prevent premature decomposition.

The range of peroxide to activator is preferably determined as a molar ratio of peroxide to activator. Thus, the range of peroxide to each activator is a molar ratio of from about 0.1:1 to 100:1, more preferably about 1:1 to 10:1 and most preferably 13 about 2:1 to 8:1. This peracid activator/peroxide composition should provide about 0.5 to 100 ppm A.O., more preferably about 1 to 50 ppm peracid A.O. (active oxygen), and most preferably about 1 to 20 ppm peracid A.O., in aqueous media for typical laundry applications. Formulations intended for hard surface cleaning will more typically have peracid activator/peroxide providing from about 0.5 to 1,000 ppm A.O., more preferably about 1 to 500 ppm peracid A.O., and most preferably about 1 to 200 ppm peracid A.O.

Delivery Systems

The activators can be incorporated into a liquid or solid matrix for use in liquid or solid detergent bleaches by dissolving into an appropriate solvent or surfactant or by dispersing onto a substrate material, such as an inert salt (e.g., NaCl, $Na_2SO_4$) or other solid substrate, such as zeolites, sodium borate, or molecular sieves. Thus, activators of the invention can be dispersed onto a solid or granulated carrier such as silica, clay, zeolite, polymer, hydrogel, starch, or ion exchange material. Alternatively, solid activator can be encapsulated such as into waxes or polymers.

Surfactants with which the activators and active oxygen compositions may be combined or admixed include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides and their ethoxylated derivatives.

Anionic surfactants may also be suitable. Examples of such anionic surfactants may include the ammonium, substituted ammonium (e.g., mono-di-, and triethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, alpha olefin sulfonates, hydroxyalkane sulfonates, fatty acid mono glyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Suitable amphoteric and zwitterionic surfactants containing an anionic water-solubilizing group, a cationic group or a hydrophobic organic group include amino carboxylic acids and their salts, amino dicarboxylic acids and their salts, alkyl-betaines, alkyl aminopropylbetaines, sulfobetaines, alkyl imidazolinium derivatives, certain quaternary ammonium compounds, certain quaternary phosphonium compounds and certain tertiary sulfonium compounds.

Other common detergent adjuncts may be added if a bleach or detergent bleach product is desired. If, for example, a dry bleaching and cleaning composition is desired, the following ranges (weight %) appear practicable:

| | |
|---|---|
| 0.5–50.0% | Active Oxygen Source |
| 0.05–25.0% | Activator |
| 1.0–50.0% | Surfactant |
| 1.0–50.0% | Buffer |
| 5.0–99.9% | Filler, stabilizers, dyes, fragrances, brighteners, etc. |

An example of a practical execution of a liquid delivery system is to dispense separately metered amounts of the activator (in some non-reactive fluid medium) and liquid hydrogen peroxide in a container such as described in Beacham et al., U.S. Pat. No. 4,585,150, issued Apr. 29, 1986. Such a dual bottle is contemplated for applications such as hard surface cleaners. It should also be understood that liquid formulations of the invention can have activator and a source of active oxygen present together so long as the pH of the solution is maintained in an acidic region, preferably between pH 0 and 4. Such a liquid formulation is storage stable. In order for activation to occur during use, such a liquid formulation will have the solution in or changed to an alkaline range, preferably a pH of about 8 to 11, and most preferably a pH of 9.5 to 11. In laundry use, this can automatically be achieved by adding such a liquid formulation to the wash, with activation occurring due to the presence of detergent as a source of alkalinity.

To summarize the single container and dual container delivery embodiments, a single container may include acetonitrile activator, surfactant, active oxygen source, and an acidic buffer (in order to stabilize the acetonitrile activator and the oxygen source (if hydrogen peroxide)). The liquid in which the just described components will be dispersed will sometimes be referred to as a "liquid matrix." This liquid matrix will include liquid (typically water) and remaining desired components such as whiteners, fragrances, colorants, stabilizers, preservatives, ionic strength adjuster, and the like. In a dual delivery embodiment, there may be one chamber containing the just described single container composition while the other chamber holds an alkaline solution. These two liquids could be combined in a third, mixing chamber of a trigger sprayer or other dispenser, or could be codelivered to a selected site, for example, as two directed fluid streams (via a pump or trigger sprayer device) to a stain on a fabric, as in a 'prewash execution, or a stain on a hard surface. In another second dual delivery embodiment, it is the source of active oxygen that is contained in a second container until the two are combined for use. A third dual delivery embodiment can have the source of active oxygen and alkaline buffer in the one container and the acetonitrile activator, surfactant, and liquid matrix in the other. Other multiple delivery options are possible.

Compositions of the invention, when combined with a source of active oxygen, preferably function for bleaching best at an alkaline pH, but are shelf stabilized best at an acidic pH. Thus, inventive compositions preferably include buffer (admixed or in a separate container) which will either be acidic, alkaline, or both, depending upon whether the delivery system is single or double. In selecting a buffer to provide an acidic pH, a mineral acid such as HCl, sulfuric, nitric, phosphoric, sulfonic, methyl sulfuric, or organic such as citric, oxalic, glutaric, acetic, benzene sulfonic, etc., are well known to the art. The alkaline buffer may be selected from sodium carbonate, sodium bicarbonate, sodium borate, sodium silicate, phosphoric acid salts, and other alkali metal/alkaline earth metal salts known to those skilled in the art. Organic buffers, such as succinates, maleates and acetates may also be suitable for use. When the composition is ready for use, it is especially advantageous to have an amount of alkaline buffer sufficient to maintain a pH greater than about 8, more preferably in the range of about 8.5 to about 10.5 for most effective bleaching.

Compositions of the invention will typically include a filler material, which in solid (e.g. granulated) compositions of the invention can be viewed as forming all or part of a matrix where the nitrile is carried by or encapsulated in the solid matrix. The filler material (which may actually constitute the major constituent by weight) is usually sodium sulfate. Sodium chloride is another potential filler.

Other adjuncts (useful in cleaning and laundering applications) are optionally included in the inventive compositions. Dyes include anthraquinone and similar blue dyes. Pigments, such as ultramarine blue (UMB), may also be used, and can have a bluing effect by depositing on fabrics washed with a detergent bleach containing UMB. Monastral colorants are also possible for inclusion. Brighteners or whiteners, such as stilbene, styrene and styrylnaphthalene brighteners (fluorescent whitening agents), may be included. Fragrances used for aesthetic purposes are commercially available from Norda, International Flavors and Fragrances and Givaudon. Stabilizers include hydrated salts, such as magnesium sulfate, and boric acid.

In some of the compositions herein, adjuvants include (and are especially preferred) a chelating agent or sequestrant, most preferably, an aminopolyphosphonate. These chelating agents assist in maintaining the solution stability of the activators and active oxygen source in order to achieve optimum performance. In this manner, they are acting to chelate heavy metal ions, which cause catalyzed decomposition of the (believed) in situ formed peroxyimidic acids, although this is a non-binding theory of their action and not limiting.

The chelating agent is selected from a number of known agents which are effective at chelating heavy metal ions. The chelating agent should be resistant to hydrolysis and rapid oxidation by oxidants. Preferably, it should have an acid dissociation constant ($pK_a$) of about 1–9, indicating that it dissociates at low pH's to enhance binding to metal cations. Acceptable amounts of the (optional) chelating agent range from 0–1,000, more preferably 5–500, most preferably 10–100 ppm chelating agent, in the wash liquor.

The most preferred chelating agent is an aminopolyphosphonate, which is commercially available under the trademark Dequest from Monsanto Company. Examples thereof are Dequest 2000, 2041f and 2060. (See also Bossu U.S. Pat. No. 4,473,507, column 12, line 63 through column 13, line 22, incorporated herein by reference.) A polyphosphonate, such as Dequest 2010, is also suitable for use.

Other chelating agents, such as ethylenediaminetetraacetic acid (EDTA) and nitrilotriacetic acid (NTA) may also be suitable for use. Still other new, preferred chelating agents are new propylene-diaminetetraacetates, such as Hampshire 1,3 PDTA, from W. R. Grace, and Chel DTPA 100#F, from Ciba Geigy A. G. Mixtures of the foregoing may be suitable.

Additional desirable adjuncts are enzymes (although it may be preferred to also include an enzyme stabilizer). Proteases are one especially preferred class of enzymes. They are preferably selected from alkaline proteases. The term "alkaline," refers to the pH at which the enzymes' activity is optimal. Alkaline proteases are available from a wide variety of sources, and are typically produced from various microorganism (e.g., *Bacillus subtilisis*). Typical examples of alkaline proteases include Maxatase and Maxacal from International BioSynthetics, Alcalase, Savinase, and Esperase, all available from Novo Nordisk A/S. See also Stanislowski et al., U.S. Pat. No. 4,511,490, incorporated herein by reference.

Further suitable enzymes are amylases, which are carbohydrate-hydrolyzing enzymes. It is also preferred to include mixtures of amylases and proteases. Suitable amylases include Rapidase, from Societe Rapidase, Milezyme from Nova Nordisk A/S, and Maxamyl from International BioSynthetics.

Still other suitable enzymes are cellulases, such as those described in Tai, U.S. Pat. No. 4,479,881, Murata et al., U.S. Pat No. 4,443,355, Barbesgaard et al., U.S. Pat. No. 4,435,307, and Ohya et al., U.S. Pat. No. 3,983,082, incorporated herein by reference.

Yet other suitable enzymes are lipases, such as those described in Silver, U.S. Pat. No. 3,950,277, and Thom et al., U.S. Pat. No. 4,707,291, incorporated herein by reference.

The hydrolytic enzyme should be present in an amount of about 0.01–5%, more preferably about 0.01–3%, and most preferably about 0.1–2% by weight of the detergent. Mixtures of any of the foregoing hydrolases are desirable, especially protease/amylase blends.

Anti-redeposition agents, such as carboxymethylcellulose, are potentially desirable. Foam boosters, such as appropriate anionic surfactants, may be appropriate for inclusion herein. Also, in the case of excess foaming resulting from the use of certain surfactants, anti-foaming agents, such as alkylated polysiloxanes, e.g. dimethylpolysiloxane, would be desirable.

Applications

Compositions of the invention are useful as or in laundry products, such as bleaching additives, detergents, detergent boosters, detergents with bleach, bleaches, bleaching aids, stain removers, and spot treatment products such as stain removers, prewash and presoak laundry aids. Among the advantages derived from compositions of the invention are improved cleaning, stain removal, spot removal, whitening, and brightening of treated articles.

Further benefits from use of the inventive compositions include scavenging of free dye during laundering to prevent dye transfer between garments (sometimes known as dye transfer inhibition).

Other product applications include household cleaning products, such as hard surface cleaners either for direct use or to be diluted with water prior to use. Exemplary surface cleaners are tile and grout cleaners, bathroom (floor, toilet, and counter) and kitchen (floor, sink, and counter) cleaners. Additionally, kitchen products such as dishwasher detergents with bleach or bleach cleaning and scrubbing pads are contemplated. Among the benefits derived from use of the inventive compositions in such applications are improved stain and spot removal and general cleaning of the treated surfaces to remove food, rust, grime, mildew, mold, and other typical stains found on such surfaces.

Additionally, non-household product applications are contemplated where an effective level of active oxygen generated in situ to treat water is useful. Illustrative of such applications are pool and spa additives, as well as cleaners to remove stains on outdoor concrete, stucco, siding, wood and plastic surfaces.

Aspects of the invention will now be illustrated by the following examples. It will be understood that these examples are intended to illustrate, and not to limit, the invention.

Formula 1 dimer embodiments of the invention may be prepared as illustrated by Examples 1 and 2.

EXAMPLE 1

1,6-Bis(4-cyanomethylmorpholinium)hexane Dichloride (HDMMA):

100 ml of morpholine (1.147 mole) and 150 ml ethylacetate (EtOAc) were added to 500 ml Morton flask equipped with reflux condenser, thermometer, mechanical stirrer, and heating mantel. 25 ml of 1,6-dichlorohexane (0.172 mole) was added slowly to flask at room temperature. This was refluxed for 48 hours. Gas chromatogram showed 90% completion of the reaction. The product 1,6-bismorpholinohexane was purified from reaction mixture by vacuum filtration to remove the morpholine hydrochloride, and the light yellow filtrate was purified by adsorption chromatography. $^{13}C$ NMR showed a spectrum consistent with structure with very minor impurities. Gas chromatography showed an approximate purity of 98.2% based upon peak areas. The collected amount of 1,6-bismorpholinehexane was 30.0 g, which corresponds to a yield of 66.6%.

12.68 g of bismorpholinohexane (0.049 mole) and 55 ml EtOAc were added to 500 ml Morton flask equipped with reflux condenser, pressure equalizing dropping funnel, mechanical stirrer, and heating mantel. 15 ml of chloroacetonitrile (0.238 mole) was added slowly to flask at room temperature. This was refluxed for 5 hours. Light brown solid precipitated from the solution, and the solid was isolated by vacuum filtration, rinsed with EtOAc, and dried overnight in vacuum oven at ambient temperature. $^{13}C$ NMR showed a spectrum consistent with structure with a significant, but small impurity of starting amine. Collected 12.6 g of product, corresponding to 57.1% yield from this step.

EXAMPLE 2

1,2-Bis(2-(4-cyanomethylmorpholinium)ethoxy) ethane Dichloride (EODMMA):

100 ml of morpholine (1.147 mole) and 150 ml EtOAc were added to 500 ml Morton flask equipped with reflux condenser, thermometer, mechanical stirrer, and heating mantel. 25 ml of 1,2-bis(2-chloroethoxy)ethane (0.160 mole) added slowly to flask at room temperature. This was refluxed for 16 hours. Product 1,2-bis(2-morpholinoethoxy) ethane was purified from reaction mixture by vacuum filtration to remove the morpholine hydrochloride, and the light yellow filtrate was purified by adsorption chromatography. 18.4 g of product was collected, and a gas chromatogram showed an approximate purity of 98.2% based upon peak areas. The collected amount of 1,2-bis(2-morpholinoethoxy)ethane corresponds to a yield of 39.2%.

14.94 g of 1,2-bis(2-morpholinoethoxy)ethane (0.051 mole) and approximately 100 ml EtOAc were added to 500 ml Morton flask equipped with reflux condenser, pressure equalizing dropping funnel, mechanical stirrer, and heating mantel. 25 ml of chloroacetonitrile (0.397 15 mole) was added slowly to flask at room temperature. This was refluxed for 8 hours. Light brown solid precipitated from the solution, and the solid was very tacky and stiff. The mechanical stirrer froze solid in the material. Mother liquor was decanted off the solid, and the solid was redissolved in methanol. The solvent was evaporated in a recrystallization dish for several days. Mother liquor reacted further for an additional 8 hours without any stirring, with more product forming. The product from the second heating was collected in a manner identical to first. 14.6 g of product was collected from the first reaction period and 5.5 g from the second reaction period. Together the two reactions yielded 20.1 g of product, corresponding to 85.4% yield. $^{13}$C NMR shows spectrum consistent with the proposed structure with a small impurity of methanol.

Preparation of a Formula 2 dimer embodiment is illustrated by Example 3.

EXAMPLE 3

Di-methylmorpholinium-glutarnitrile (DCDMG):

Dissolve 45.15 g (0.1465 mole) of sodium bisulfate addition complex of glutaraldehyde [28959-35-5] in approximately 130 mL of water. Separately, dissolve potassium cyanide (19.46 g, 0.2989 mole) in about 50 mL of water. Prepare a separate, 25% aqueous solution of morpholine containing 28.08 grams of morpholine (0.3233 mole). The morpholine solution is added to the stirring solution of the glutaraldehyde bisulfate addition complex, which is then cooled in an ice-bath. Next, the potassium cyanide solution is slowly added with stirring. After addition is complete, the flask is allowed to come to room temperature and left to stir overnight. The resulting solid suspension is filtered and the filter cake is washed well with water. Damp filter cake is then dried in a vacuum oven to give 39.32 grams of a white solid (92% yield). An analytical sample can be recrystallized from ethanol/water to give white crystals. [Note: all of the aqueous washings from the above reactions are treated with 5.25% sodium hypochlorite to destroy any remaining cyanide.]

Place 15.0 g (0.0513 mole) of 1,5-dicyano-1,5-morpholinopentane in a 100 mL round-bottom flask. Fit with nitrogen line and overhead mechanical stirrer. Slowly add dimethyl sulfate (41.0 g, 0.3251 mole) with stirring. Heat to 50° C. with continuous stirring for three hours. Cool to room temperature. Add ethanol and break up solid in a mortar and pestle. Filter. Suspend solid in 500 mL methanol and heat to boiling. Cool slowly to room temperature, and then in ice-bath. Filter and wash filter cake with methanol. Dry solid in vacuum oven to give 16.9 g white solid.

EXAMPLE 4

A dimeric embodiment of the invention prepared as described by Example 3 was tested for active oxygen yield in comparison with three comparative compounds. Thus, the inventive embodiment DCDMG and three comparative compounds DMMA, MMP, and MAN were also tested for active oxygen. As seen from Table 1, and in stark contrast to the inventive compound, the three comparative compounds gave no or virtually no active oxygen yield, while DCDMG yielded 135%.

TABLE 1

| Structure | Name | Active Oxygen Yield |
|---|---|---|
| [structure with two cyanomethyl morpholinium groups connected by propylene chain] | DCDMG (di-methyl-morpholinium-glutarnitrile) (inventive) | 67% of theoretical |
| [morpholinium with methyl and CN substituents] | DMMA (dimethyl-morpholinium methylsulfate) | None detected |
| [N-methyl morpholinium with CN group] | MMP (methyl-morpholinium propionitrile) | None detected |
| [morpholine with CN group] | MAN (morpholine acetonitrile) | 1% |

The Table 1 compounds were tested for active oxygen yield by a standard test procedure as follows. A sodium carbonate buffer is prepared with the pH adjusted to 10.5 and often optionally contains a very low concentration of a metal sequestrant to approximate the laundry wash water mixture. (Although surfactants are usually omitted from this testing stage.) Hydrogen peroxide is added by micropipette as a source of active oxygen to a 200 ml volume of the buffer, and the candidate activator is added as either a predissolved solution or as the neat compound. On a molar basis, hydrogen peroxide is usually in ~2-fold excess relative to the activator. As the reaction in aqueous solution proceeds, samples of the solution are removed from the mix. The samples are typically 50 ml, and the enzyme catalase is added to the aliquot to eliminate the excess hydrogen peroxide. The remaining active oxygen in solution, now associated only with the activator or its intermediate, is titrated iodometrically. That is, sulfuric acid and potassium iodide are added, and the iodine generated by reaction of the active oxygen with iodide is titrated with sodium thiosulfate to a starch endpoint. Alternatively, the iodine can be detected electrochemically. Both techniques have been used.

EXAMPLE 5

Inventive compounds are particularly contemplated as activators in bleaching applications. Therefore, a desired property of these compounds is that of exhibiting perhydrolysis when combined with hydrogen peroxide. As summarized by the data in Table 2, titrated perhydrolysis yields with excess hydrogen peroxide present (as determined by electrochemical analyzer with response standardized against oxone or peroxide standard solution) were performed for two preferred embodiments of the invention.

TABLE 2

| Name | Titrated % Yield |
|---|---|
| 1,6-di(4-Cyanomethylmorpholinium)hexane Dichloride (HDMMA) | 40 |
| 1,2-bis(2-(4-Cyanomethyl-morpholinium)ethoxy)ethane dichloride (EODMMA) | 20 |

Bleaching compositions of the invention include a source of active oxygen. The source of active oxygen itself constitutes a bleaching agent; however, bleaching compositions of the invention that include the inventive nitrites as activators, together with a source of active oxygen, provide enhanced bleaching with respect to the oxygen source by itself.

It is to be understood that while the invention has been described above in conjunction with preferred specific embodiments, the description and examples are intended to illustrate and not limit the scope of the invention, which is defined by the scope of the appended claims.

It is claimed:

1. A bleaching or cleaning composition, comprising:

a dimeric N-alkyl ammonium acetonitrile having two monomeric units, each monomeric unit with a cyano group and a saturated ring of which a quaternized nitrogen atom is a part, each cyano group being bonded to the quaternized nitrogen atom through a single carbon atom having a hydrogen substituent thereon, wherein the dimeric acetonitrile has the structure of Formula 2

FORMULA 2

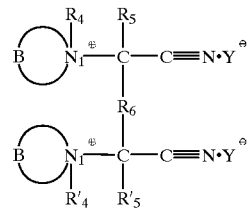

where the substituents $R_4$ and $R'_4$ bound to the $N_1$ atom of the Formula 2 structure are the same or different and are (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) a $-CR_2R_3C\equiv N$, where at least one of the $R_2$ and $R_3$ substituents is H and the other of $R_2$ and $R_3$ is H, a $C_{1-24}$ alkyl, cycloalkyl, or alkaryl, or a repeating or nonrepeating alkoxyl or alkoxylated alcohol where the alkoxy unit is $C_{2-4}$, $R_5$, and $R'_5$ are each H, a $C_{1-24}$ alkyl, cycloalkyl, or alkaryl, or a repeating or nonrepeating alkoxyl or alkoxylated alcohol where the alkoxy unit is $C_{2-4}$, $R_6$ is an alkylene $-[CH_2]_n-$ where n is 1 to about 15, B has six atoms including the $N_1$ atom and optionally contains at least one carbon atom and at least one of O, S, and N, and wherein Y is a counterion; and a source of active oxygen, the dimeric acetonitrile and the active oxygen together providing enhanced bleaching with respect to the oxygen source by itself.

2. The bleaching or cleaning composition as in claim 1 wherein the cyclic configuration B has six atoms including the $N_1$.

3. The bleaching or cleaning composition as in claim 2 wherein the cyclic configuration B includes an oxygen atom.

4. The bleaching or cleaning composition as in claim 1 wherein $R_4$ and $R'_4$ are both a $C_{1-8}$ alkyl.

5. The bleaching or cleaning composition as in claim 1 wherein Y is chloride, bromide, nitrate, alkyl sulfate, bisulfate, sulfate, tosylate, and mixtures thereof.

6. The bleaching or cleaning composition as in claim 1 wherein at least one of $R_5$ and $R'_5$ is H.

* * * * *